(12) United States Patent
Lovejoy et al.

(10) Patent No.: US 11,426,444 B2
(45) Date of Patent: Aug. 30, 2022

(54) COMPOSITIONS, METHODS AND USES FOR TREATING POST-TRAUMATIC STRESS DISORDER

(71) Applicants: David Lovejoy, Stouffville (CA);
Robert Stein, New York, NY (US);
Andrew Slee, Shrewsbury, MA (US);
Garo Armen, New York, NY (US)

(72) Inventors: David Lovejoy, Stouffville (CA);
Robert Stein, New York, NY (US);
Andrew Slee, Shrewsbury, MA (US);
Garo Armen, New York, NY (US)

( * ) Notice: Subject to any disclaimer, the term of this patent is extended or adjusted under 35 U.S.C. 154(b) by 0 days.

(21) Appl. No.: 16/755,372

(22) PCT Filed: Oct. 12, 2018

(86) PCT No.: PCT/US2018/055732
§ 371 (c)(1),
(2) Date: Apr. 10, 2020

(87) PCT Pub. No.: WO2019/075416
PCT Pub. Date: Apr. 18, 2019

(65) Prior Publication Data
US 2020/0246421 A1  Aug. 6, 2020

Related U.S. Application Data

(60) Provisional application No. 62/571,616, filed on Oct. 12, 2017.

(51) Int. Cl.
| | | |
|---|---|---|
| *A61K 38/17* | (2006.01) |
| *A61K 38/00* | (2006.01) |
| *A61P 25/22* | (2006.01) |
| *A61P 25/24* | (2006.01) |
| *A61P 25/26* | (2006.01) |
| *C07K 14/00* | (2006.01) |

(52) U.S. Cl.
CPC .............. *A61K 38/17* (2013.01); *A61P 25/22* (2018.01)

(58) Field of Classification Search
CPC ......... A61K 38/17; A61K 38/00; A61P 25/22; A61P 25/24; A61P 25/26; C07K 14/00; C07K 14/435

USPC .................. 514/2, 17.5, 17.6, 17.7; 530/324
See application file for complete search history.

(56) References Cited

U.S. PATENT DOCUMENTS

2006/0035318 A1   2/2006  Lovejoy
2008/0318854 A1  12/2008  Lovejoy

OTHER PUBLICATIONS

Posttraumatic Stress Disorder from Merck Manual, pp. 1-3. Accessed Mar. 17, 2021. (Year: 2021).*
PCT Search Report & Written Opinion dated Jan. 22, 2019, Application No. PCT/US2018/055732.
Liqun Wang et al: "Teneurin proteins possess a carboxy terminal sequence with neuromodulatory activity", Molecular Brain Research, vol. 133, No. 2, Feb. 1, 2005, pp. 253-265, XP055540792.
Laura A. Tan et al: "Repeated intracerebral teneurin C-terminal associated peptide (TCAP)-1 injections XP055540793produce enduring changes in behavioral responses to corticotropin-releasing factor (CRF) in rat models of anxiety", Behavioural Brain Research, vol. 188, No. 1, Mar. 1, 2008, pp. 195-200.
Laura A. Tan et al: "Teneurin C-terminal associated peptide (TCAP)-1 modulaltes dendritic morphology in hippocampal neurons and decreases anxiety-like behaviors in rats", Physiology and Behavior, vol. 104, No. 2, Aug. 1, 2011, pp. 199-204, XP055540795.
Rebecca Woelfle et al: "Teneurins, TCAP, and latrophilins: roles in the etiology of mood disorders", Translational Neuroscience, vol. 7, No. 1, Jan. 1, 2016, pp. 17-23, XP055540802.
Tan L A et al: "Teneurin C-terminal associated peptide (TCAP)-1 attenuates corticotropin-releasing factor (CRF)—induced c-Fos expression in the limbic system and modulates anxiety behavior in male Wistar rats", Behavioural Brain Research, Elsevier, Amsterdam, NL, vol. 201, No. 1, Jul. 19, 2009, pp. 198-206, XP026020931.
Al Chawaf et al. "Corticotropin-releasing factor (CRF)—induced behaviors are modulated by intravenous administration of teneurin C-terminal associated peptide-1 (TCAP-1)", Peptides, Elsevier, Amsterdam, NL, vol. 28, No. 7, Jul. 26, 2007, pp. 1406-1415, XP022168929.

* cited by examiner

*Primary Examiner* — Julie Ha
(74) *Attorney, Agent, or Firm* — The Dobrusin Law Firm, PC

(57) ABSTRACT

Compositions comprising a Teneurin C-terminal Associated Peptide—1 (TCAP-1) peptide are described with respect to methods and uses of same for preventing and/or treating post-traumatic stress disorder ("PTSD").

6 Claims, 13 Drawing Sheets
Specification includes a Sequence Listing.

| | |
|---|---|
| 38 | Mouse TCAP 1 (41)<br>Gln Gln Leu Leu Gly Thr Gly Arg Val Gln Gly Tyr Asp Gly Tyr Phe<br>Val Leu Ser Val Glu Gln Tyr Leu Glu Leu Ser Asp Ser Ala Asn Asn<br>Ile His Phe Met Arg Gln Ser Glu Ile (SEQ. ID. NO. 1) |
| 70 | Human TCAP 1 (41)<br>Gln Gln Leu Leu Ser Thr Gly Arg Val Gln Gly Tyr Asp Gly Tyr Phe<br>Val Leu Ser Val Glu Gln Tyr Leu Glu Leu Ser Asp Ser Ala Asn Asn<br>Ile His Phe Met Arg Gln Ser Glu Ile (SEQ. ID. NO. 2) |
| 101 | G. Gallus TCAP-1 (41)<br>Gln Gln Leu Leu Asn Thr Gly Arg Val Gln Gly Tyr Asp Gly Tyr Phe<br>Val Leu Ser Val Glu Gln Tyr Leu Glu Leu Ser Asp Ser Ala Asn Asn<br>Ile His Phe Met Arg Gln Ser Glu Ile (SEQ. ID. NO. 3) |

Figure 1

SEQUENCE LISTING

```
<160> NUMBER OF SEQ ID NOS: 9

<210> SEQ ID NO 1
<211> LENGTH: 41
<212> TYPE: PRT
<213> ORGANISM: Artificial Sequence
<220> FEATURE:
<223> OTHER INFORMATION: Mouse TCAP1 (41 a.a.)

<400> SEQUENCE: 1

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 2
<211> LENGTH: 41
<212> TYPE: PRT
<213> ORGANISM: Artificial Sequence
<220> FEATURE:
<223> OTHER INFORMATION: Human TCAP1 (41 a.a.)

<400> SEQUENCE: 2

Gln Gln Leu Leu Ser Thr Gly Arg Val Gln Gly Tyr Asp Gly Tyr Phe
1               5                   10                  15
```

```
Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 3
<211> LENGTH: 41
<212> TYPE: PRT
<213> ORGANISM: Artificial Sequence
<220> FEATURE:
<223> OTHER INFORMATION: G. gallus TCAP-1

<400> SEQUENCE: 3

Gln Gln Leu Leu Asn Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 4
<211> LENGTH: 40
<212> TYPE: PRT
<213> ORGANISM: Artificial Sequence
<220> FEATURE:
<223> OTHER INFORMATION: Mouse TCAP1 (40 a.a.)

<400> SEQUENCE: 4

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 5
<211> LENGTH: 43
<212> TYPE: PRT
<213> ORGANISM: Artificial Sequence
<220> FEATURE:
<223> OTHER INFORMATION: Mouse preTCAP1 (43 a.a.)

<400> SEQUENCE: 5

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35                  40

<210> SEQ ID NO 6
<211> LENGTH: 44
<212> TYPE: PRT
<213> ORGANISM: Artificial Sequence
<220> FEATURE:
<223> OTHER INFORMATION: Mouse preTCAP1 (44 a.a.)

<400> SEQUENCE: 6

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30
```

```
Ile His Phe Met Arg Gln Ser Glu Ile Gly Arg Arg
        35                  40

<210> SEQ ID NO 7
<211> LENGTH: 40
<212> TYPE: PRT
<213> ORGANISM: Artificial Sequence
<220> FEATURE:
<223> OTHER INFORMATION: Human TCAP1 (40 a.a.)

<400> SEQUENCE: 7

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 8
<211> LENGTH: 43
<212> TYPE: PRT
<213> ORGANISM: Artificial Sequence
<220> FEATURE:
<223> OTHER INFORMATION: Human preTCAP1 (43 a.a.)

<400> SEQUENCE: 8

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35                  40

<210> SEQ ID NO 9
<211> LENGTH: 44
<212> TYPE: PRT
<213> ORGANISM: Artificial Sequence
<220> FEATURE:
<223> OTHER INFORMATION: Human preTCAP1 (44 a.a.)

<400> SEQUENCE: 9

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile Gly Arg Arg
        35                  40
```

COMPOSITIONS, METHODS AND USES FOR TREATING POST-TRAUMATIC STRESS DISORDER

CROSS-REFERENCE TO RELATED APPLICATIONS

This application claims the benefit and priority of U.S. Provisional Patent Application No. 62/571,616 filed Oct. 12, 2017 and entitled "Compositions, Methods and Uses for Treating Post-Traumatic Stress Disorder". This reference is incorporated in its entirety herein by reference.

FIELD OF THE INVENTION

The present invention relates to compositions, methods and uses of Teneurin C-Terminal Associated Peptide—1 (a TCAP-1 peptide) as a treatment for Post-Traumatic Stress Disorder ("PTSD").

BACKGROUND OF THE INVENTION

Post-Traumatic Stress Disorder (PTSD) is included in a distinct category in the American Psychiatric Association's Diagnostic and Statistical Manual for Mental Disorders (DSM-5), under Trauma- and Stressor-Related Disorders. All of the conditions included in this classification require exposure to a traumatic or stressful event as a diagnostic criterion.

PTSD causes changes in the brain and body, which differ and are distinct from other psychiatric disorders such as major depression and anxiety (such as general anxiety). Individuals diagnosed with PTSD respond more strongly to a dexamethasone suppression test than individuals diagnosed with clinical depression. (Yehuda et al, 2004; Yehuda et al, 2002).

Numerous factors influence treatment outcomes, and no single treatment to date has been demonstrated to be effective for everyone who has PTSD. It has been suggested that about 33% of people in the general population who have PTSD are resistant to current treatments. (Institute of Medicine. Washington (DC): National Academies Press (US); 2014 Jun. 17).

As such there is a need for treatments for PTSD.

SUMMARY OF THE INVENTION

The present invention provides a teneurin c-terminal associated peptide-1 as described herein (TCAP-1 peptide) and compositions comprising same for methods and uses for preventing and/or treating PTSD.

In some embodiments, the invention provides a method for treating PTSD, comprising administering to a patient or subject in need thereof a therapeutically effective amount of a teneurin c-terminal associated peptide-1 (TCAP-1), SEQ ID NOs: 1, 2 or 3 (TCAP-1 peptide), or a pharmaceutically acceptable salt or ester thereof or a pharmaceutical composition comprising same, wherein the amino acid sequence of said TCAP-1 peptide consists essentially of:
  (i) an amino acid sequence of SEQ ID NOs: 1, 2 or 3 or having at least 95% identity to an amino acid sequence selected from the group consisting of SEQ ID NOs: 1, 2 or 3 or a species homolog thereof;
  optionally wherein:
  (a) the carboxy terminal end of said TCAP peptide is amidated or comprises an amidation signal sequence, such as GRR; and/or
  (b) when the amino terminal amino acid of said TCAP peptide is glutamine, it is in some embodiments in the form of pyroglutamic acid.

In some other embodiments, the invention provides a method for preventing and/or treating a PTSD disorder by administration of a therapeutically effective amount of a TCAP-1 peptide or a pharmaceutical composition comprising a TCAP-1 peptide, as TCAP-1 peptide is described herein to a patient or subject.

In some embodiments, a TCAP-1 peptide and compositions comprising same, can be used to treat PTSD.

In a third aspect, the present invention provides a TCAP-1 peptide and compositions comprising same for the therapeutic use in treating or preventing disorders associated with PTSD, such as intrusive memories, avoidance, negative changes in thinking and mood, and changes in physical and emotional reactions.

In some embodiments the patient or subject is a mammal. In some other embodiments, the mammal is selected from the group consisting of humans, dogs, cats, rodents, horses, sheep and cattle. In some embodiments, the patient or subject is human.

Additional aspects and advantages of the present invention will be apparent in view of the description which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In order that the subject matter may be readily understood, embodiments are illustrated by way of examples in the accompanying drawings, in which:

FIG. 1 is the TCAP-1 SEQ ID Nos: 1-3 for mouse, human and *G. gallus*, respectively.

DETAILED DESCRIPTION OF THE INVENTION

Figures 2, 3:
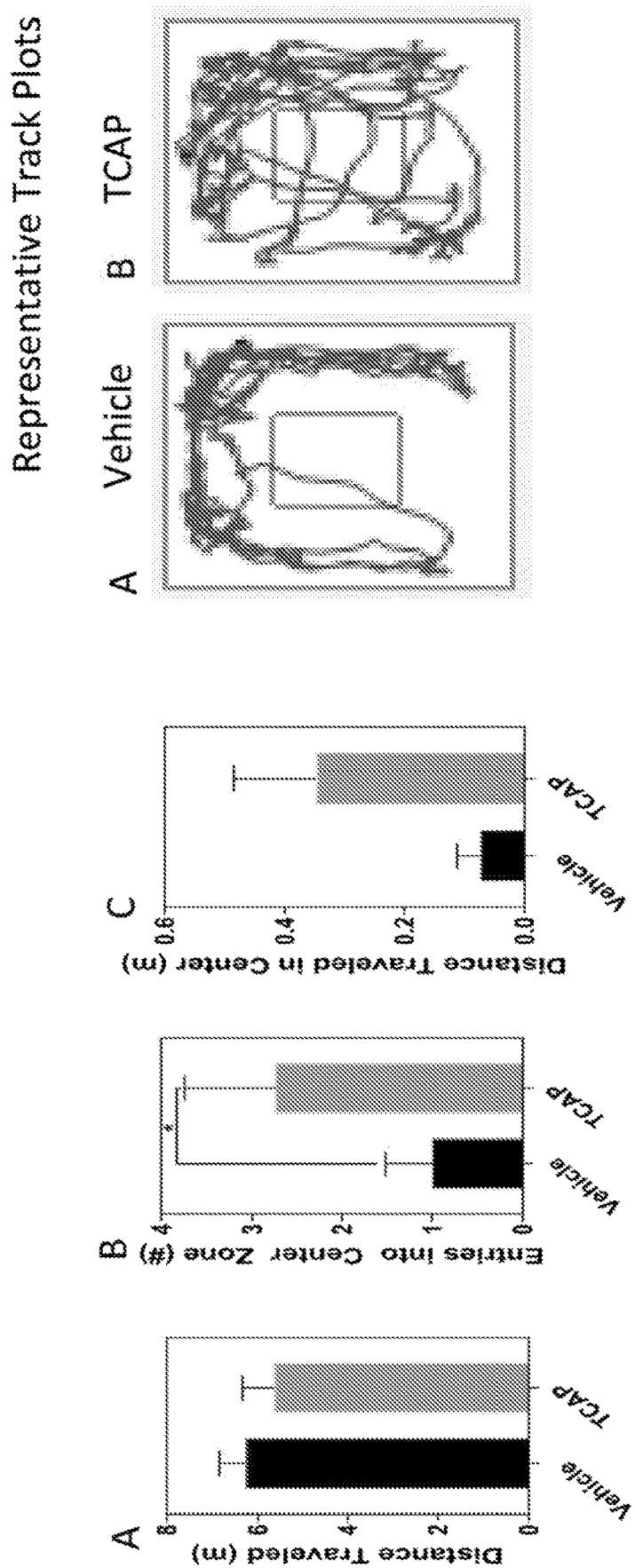
FIG. 2 are bar graphs of: (A) distance travelled; (B) entries into the centre zone; and (C) distance travelled in centre zone of animals treated with vehicle and TCAP-1 who were exposed to a traumatic event (noise pollution).
FIG. 3 are actual representative movement plots of the animals treated with: (A) vehicle and (B) TCAP-1.

Teneurin C-terminal associated peptides (TCAPs 1-4) are four paralogous bioactive peptides located at the distal extracellular end of each teneurin transmembrane protein. First described by Lovejoy et al and described in U.S. Pat. No. 8,088,889, which is herein incorporated by reference. TCAP-1 can be independently transcribed and has biological actions distinct from the teneurins, demonstrating functional independence from its proprotein. It has a unique mechanism of action. ADGRL (Latrophilin), an adhesion G protein—coupled receptor (GPCR), has recently been identified as part of the ligand-receptor complex that binds the teneurin/TCAP system. Previously elucidated in neurons, the teneurin/TCAP-ADGRL complex is associated with glucose metabolism; however, it is not well understood in other tissues.

PTSD has been linked with a dysregulation of the glutamate system. Individuals with PTSD show a higher concentration of glutamate in the right hippocampus compared to trauma-exposed individuals without PTSD (Rosso et al 2017). Higher glutamate concentrations are also found in the dorsal anterior cingulate cortex of PTSD patients compared to those without PTSD (Harnett et al 2017). Analysis of the human cortices has also shown that levels of metabotropic glutamate receptor 5 (mGlutR5) are significantly increased in the dorsolateral prefrontal cortex and orbitofrontal cortex of PTSD patients compared to those of healthy individuals (Holmes et al 2017). Post-mortem analysis of human prefrontal cortex tissue showed higher mRNA expression of SHANK1, a protein that serves to anchor mGluR5 to the cell membrane, in those with PTSD compared to healthy controls as well. Furthermore, brain glutamate levels have been positively correlated with posttraumatic diagnostic scale (PSD) scores and severity of PTSD symptoms such as avoidance, arousal and re-experiencing in both acute and long-term evaluations (Harnett et al, 2017; Rosso et al 2017). Cortical levels of mGluR5 have also been positively correlated with avoidance symptom severity in PTSD patients (Holmes et al 2017).

Definitions

"Preventing" as used herein in reference to preventing PTSD or PTSD onset means, in the context of administering a TCAP-1 peptide to a patient, post-traumatic event(s) to minimize risk of developing PTSD.

"Post-Traumatic Stress Disorder" or "PTSD" as used herein means the disorder as described in the American Psychiatric Association (2013). Diagnostic and Statistical Manual of Mental Disorders (Fifth ed.) (DSM-5), which is herein incorporated by reference and includes expression for over one (1) month of debilitating symptoms from four clusters following exposure to traumatic events such as actual or threatened death, or actual or threatened serious injury or violence (e.g. sexual violence):

Cluster B: Intrusion (e.g. nightmares, flashbacks, intrusive through, and physiological reactions to trauma reminders).

Cluster C: Avoidance (e.g., intentionally avoiding trauma-related people, places or activities).

Cluster D: Negative alterations in cognitions and mood (e.g., dissociative amnesia, negative perception of self and world, anhedonia, social withdrawal).

Cluster E: Alterations in arousal and reactivity (e.g., irritability, aggression, problems concentrating, sleep disturbances, and hypervigilance). [See also Flandreau, Elizabeth I. et al., "Animal Models of PTSD; A Critical Review, Curr Topics Behav Neurosci (2018) 38:47-68, incorporated herein by reference.]

"Stressor" or "Traumatic Event" as used herein means an event or events that involved actual or threatened death or serious injury, or a threat to the physical integrity of self or others (including actual or threatened sexual violence) and includes the definition of traumatic event in DSM-5 for PTSD.

"Therapeutically Effective Amount" as used herein when applied to dose or amount refers to that quantity of a compound or pharmaceutical composition that is sufficient to result in a desired activity upon administration to a living animal body. It is understood that a therapeutic amount may vary depending on a number of factors, including but not limited to gender, weight, body mass or body surface area, severity of a condition, age (e.g., child, teen, adult, or senior).

"Treating" or "treatment" as used herein in the context of PTSD means alleviating or controlling or managing the symptoms of PTSD and not necessarily "curing" or "curing permanently" PTSD, but can also include same.

DESCRIPTION

Post-Traumatic Stress Disorder (PTSD), a spectrum of maladaptive mental and behavioral responses to severe or chronic stress, is a major unmet medical need and is especially prevalent in combat veterans. Current treatments for PTSD are suboptimal with regard to efficacy, side effects, or both. Corticotrophin releasing hormone (CRH), a hypothalamic neuropeptide, plays a central role in mental and behavioral responses to environmental stress. CRH is overproduced in PTSD, and PTSD sufferers appear to be more sensitive to the actions of CRH.

Although TCAP and teneurins have been largely studied in the brain and shown to have normalizing effects on stressed or high and low anxiety animals (See U.S. Pat. No. 8,088,889, which is herein incorporated by reference). The TCAP, portion of teneurin proteins, blocks CRH activities through a separate receptor called latrophilin and synthesized TCAP given to rodents reverses stress-induced behavioral dysfunction, including anxiety, depression, and drug addiction (e.g., it counteracts CRH effects to normalize stress-mediated depression, anxiety, and addiction behaviors when given to rodents). It has better relief of illness in current responders and greater efficacy in current non-responders with fewer side effects, e.g. less sedation, less harmful pharmacology and less dependency.

TCAP-1 calms anxious behavior without sedation or evidence of dependency, which would be an important advance over Valium and other benzodiazepine anti-anxiety drugs. Its anti-depressant effects have rapid onset of action, a medically meaningful distinction from Prozac, Effexor and other neurotransmitter reuptake inhibitors. These pharmaceuticals have many side effects and require a month or longer to exert their effects, during which the patient remains vulnerable. As an intervention in drug addiction, TCAP-1 reduces drug seeking behavior in rodents without interfering with reward circuitry to depress mood, making it a potential replacement or complement to suboxone for opioid addiction. The pharmacological benefits of TCAP-1 administration persist for significant periods after one dose, reflecting its ability to restore long-term balance to brain function.

TCAP-1 had been evaluated in models of depression (e.g. force swim) and anxiety (e.g. open field). However, no studies were previously done in a PTSD model which is a separate disorder. The inventors herein show the specific role of TCAP-1 in a PTSD model. Such models have been accepted as translational to humans (see Flandreau, Elizabeth I. et al., "Animal Models of PTSD; A Critical Review, Curr Topics Behav Neurosci (2018) 38:47-68, incorporated herein by reference).

PTSD

The present inventors have conducted experiments to show that TCAP-1 would work on PTSD. A neural circuitry that is essential to the etiology of PTSD in humans, is highly conserved throughout evolution, and because PTSD is precipitated by a definite traumatic experience, animal models can simulate the induction of PTSD. (See Flandreau et al., 2018).

At least 5 different criteria can be used to grade how comparable a model is to PTSD, including: very brief stressors induce biological or behavioural symptoms of PTSD; the stressor is capable of producing symptoms in a dose-dependent manner; produced biological alterations persist or become more pronounced over time; alterations have potential for bidirectional expression of biobehavioural changes; and inter-individual variability in response is present as function of experience.

Further there are model systems that have been accepted as having validity to human PTSD, (Flandreau et al., 2018) including restraint stress and social defeat.

Restraint Stress (RS):

Restraint by itself is used to generate PTSD-like anxiety in the RS model. Animals generally are placed in a plastic restraint device, for a duration between 15 min and 2 h at a time. Studies using this model demonstrated increased negative HPA feedback similar to that observed in PTSD.

Social Defeat:

In the social defeat (SD) model, subjects are exposed to and suppressed by a single aggressor animal. Suppressed animals can be categorized as either susceptible or resilient, and while both express anxiety-like behaviour, only the susceptible population shows increased avoidance.

Teneurin C-Terminal Associated Peptide-1 (TCAP-1)

TCAP-1 as used herein is a peptide that consists of a sequence found at the c-terminal of a Teneurin M-1 peptide, more particularly described below (and collectively referred to as "TCAP-1 peptide"). There is considerable cross-species homology.

In some embodiments the TCAP-1 peptide ("TCAP-1") is a 41-mer peptide selected from SEQ ID Nos: 1 to 3 (see also FIG. 1). In some embodiments it is an amidated peptide, (such as a C-terminal amidated peptide and/or having an amidation signal sequence, such as GRR), in some other embodiments the TCAP has a pyroglutamic acid at the N-terminal. In other embodiments, it has both a pyroglutamic acid at the N-terminal and is amidated at the C-terminal.

In other embodiments it is a human TCAP-1. In some embodiments it is a 41-mer c-terminal amidated peptide consisting of the following sequence (SEQ ID NO: 2):

```
Amidated Human TCAP-1 (41 mer)
Gln* Gln Leu Leu Ser Thr Gly Arg Val Gln Gly Tyr Asp Gly Tyr Phe Val Leu Ser Val Glu Gln Tyr Leu Glu Leu Ser Asp Ser Ala Asn Asn Ile His Phe Met Arg Gln Ser Glu Ile-NH2
```

* In some embodiments the N-terminal glutamic acid may be a pyroglutamic acid.

In some other embodiments, the peptide used is a salt, ester, solvate, polymorph or enantiomers of SEQ ID Nos: 1 to 3, in some embodiments SEQ ID NO: 1, or any amidated or pyroglutamic acid or amidated and pyroglutamic acid form of SEQ ID Nos: 1 to 3.

In some other embodiments, conservative substitutions or modifications can be made to the peptide sequence which does not affect its structure or function and thus could be used for the present invention, such as various species homologs. For instance those present in species homologs, such as the mouse, human or *G. gallus* TCAP-1 sequences (SEQ ID Nos: 1-3) where the fifth amino acid may be selected from: Gly, Asn or Ser. In some embodiments, the peptide has 95% identity to SEQ ID Nos: 1, 2, or 3. There is a high degree of homology amongst species, for instance the mouse TCAP-1 (*Mus musculus*) has the same sequence as the rat TCAP-1 (*Rattus norvegicus*), while the human TCAP-1 and that of the long-tailed Macaque (*Macaca fascicularis*) are the same.

Pharmaceutical Compositions

The present invention contemplates the administration of a pharmaceutical composition comprising a TCAP-1 peptide as described herein (including an amidated and/or pyroglutamic acid form of TCAP-1 or a peptide with 95% identity to SEQ ID Nos: 1-3 as shown in FIG. 1) and a pharmaceutically acceptable carrier.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia (USP), National Formulary (NF), or other generally recognized pharmacopeia for use in mammals, and more particularly in humans. Active Pharmaceutical Ingredients (APIs) of the present invention may be in the form of pharmaceutically acceptable salts. "Pharmaceutically acceptable salts" refers to those salts which possess the biological effectiveness and properties of the parent compound and which are not biologically or otherwise undesirable.

The pharmaceutical compositions of the present invention may comprise one or more excipients. Excipients which may be used include carriers, surface active agents (surfactants), thickening (viscosity) agents, emulsifying agents, binding agents, dispersion or suspension agents, buffering agents, penetration-enhancing agents, solubilizers, colorants, sweeteners, flavoring agents, coatings, disintegrating agents, lubricants, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

The term "carrier" applied to pharmaceutical compositions of the invention refers to a diluent, excipient, or vehicle with which an active compound is administered. Such pharmaceutical carriers can be liquids, such as water, saline solutions, aqueous dextrose solutions, aqueous glycerol solutions, and lipids and oils, including those of petroleum, animal, vegetable or synthetic origin. Suitable pharmaceutical carriers are described in "Remington's Pharmaceutical Sciences" by E. W. Martin, 18.sup.th Edition.

In some embodiments, the dosage form is a subcutaneous dosage form. This differs from direct administration to the brain, amygdala, or Intracerebroventricular ("ICV"). Subcutaneous administration has many advantages over direct administration to the brain.

In some embodiments as in the composition used in the Examples, the composition dissolves an amidated and pyroglutamic acid form of TCAP in a saline solution and is subcutaneously administered into animals (not ICV or amygdala). This formulation has advantages over prior forms for delivery, i.e., ICV or amygdala, in that it does not require additional sedatives, or the like for administration. In other embodiments, the formulation is an oral (buccal or sublingual) or nasal formulation.

The compositions may, if desired, be presented in a pack or dispenser device which may contain one or more unit dosage forms containing the active ingredient(s). The pack may, for example, comprise metal or plastic foil, such as a blister pack. Compositions of the invention formulated in a compatible pharmaceutical carrier may also be prepared, placed in an appropriate container, and labeled for treatment of an indicated condition.

In some embodiments, TCAP-1 and the pharmaceutical compositions of the invention are used to prevent or treat PTSD in an animal, in some embodiments mammals, including but not limited to humans, dogs, cats, horses, sheep, cattle.

Methods and Uses

In some embodiments, a TCAP-1 peptide and the pharmaceutical compositions comprising same can prevent or treat PTSD, or assist in controlling symptoms of PTSD. In some embodiments it can be used (or administered to a patient) before (e.g. an anticipated traumatic event), during or after a traumatic event.

In some embodiments the TCAP-1 peptide and pharmaceutical compositions comprising same of the present invention can be used in methods for treating or preventing PTSD or PTSD symptoms by administering an effective amount of TCAP-1 to a patient in need thereof, before, during or after a traumatic event or stressor or anticipated traumatic event or stressor.

In some embodiments various doses can be used. Therapeutically effective doses can vary based on body size, age, sex, etc. . . . . Further, when referring to animal doses there are various known practices for converting to human doses, such as Nair et al 2016.

The present invention is described in the following Examples, which are set forth to aid in the understanding of the invention, and should not be construed to limit in any way the scope of the invention as defined in the claims which follow thereafter.

EXAMPLES

The following examples illustrate the role of TCAP-1 in preventing and treating PTSD and/or symptoms of PTSD.

Materials and Methods

TCAP-1 Composition

Figure 14:
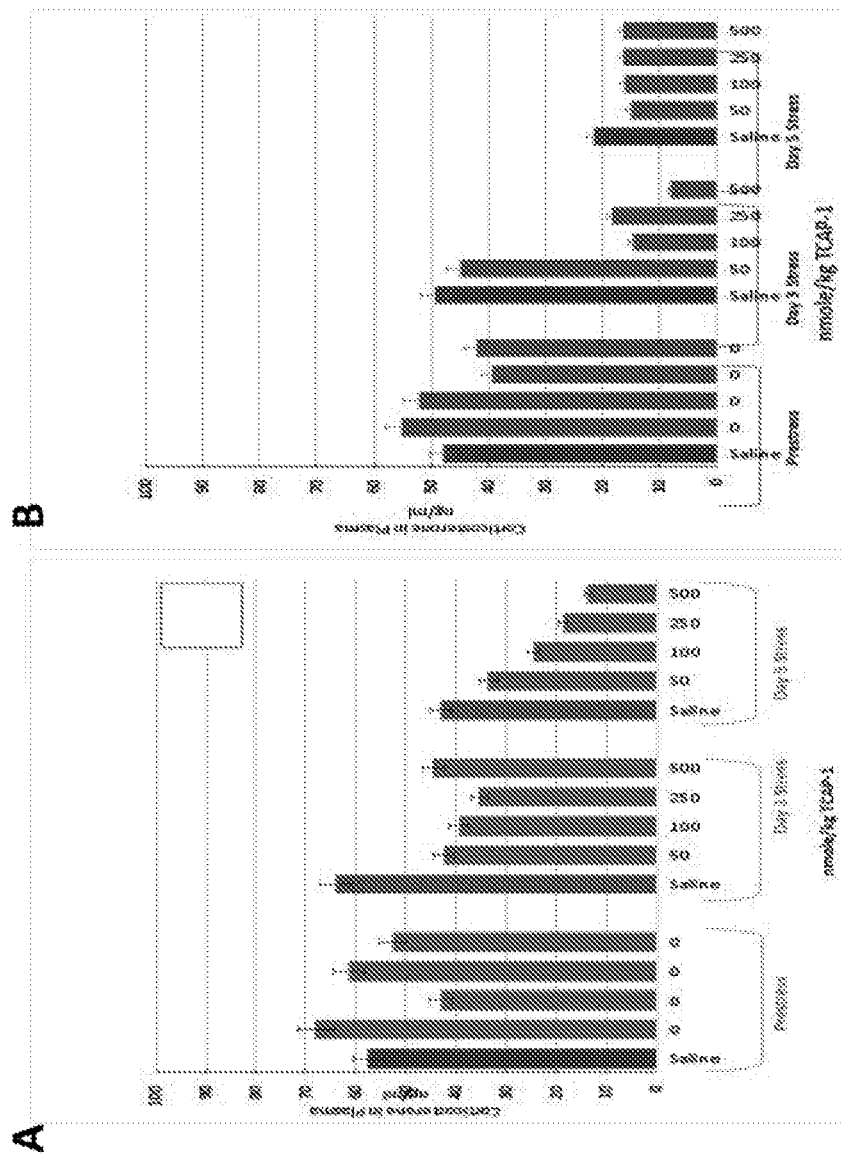
FIG. 14 is a bar graph illustrating the results of Example 7 the restraint stress model and effects on corticosterone levels in (A) Swiss Webster (SW) male mice and (B) Sprague-Dawley (SD) male rats.

Amidated mouse TCAP-1 (SEQ ID NO: 1) was suspended in 0.9% saline. [10 nmol/Kg, Ambiopharm] for subcutaneous injection in the interscapular region and used in Examples 1, Amidated human TCAP-1 (SEQ ID NO: 2) was suspended in 0.9% saline. [10 nmol/Kg, Ambiopharm] was used in Example 7, for the SD-rat (FIG. 14 B).

Amidated TCAP-1 peptide used in the composition was synthesized on an automated peptide synthesizer, Model Novayn Crystal (NovaBiochem) on PEG-PS resin using continuous flow Fmoc chemistry (Calbiochem-NovabiochemGroup). Eight times excess diisopropyl ethyl amine (Sigma-Aldrich) and four times excess Fmoc-amino acid activated with HATU (O-(7-azabenzotriazol)-1-3, 3-tetramethyluroniurn hexfluorophosphate; Applied Biosystems) at a 1:1 (mol/mol) ratio were used during the coupling reaction. The reaction time was 1 h. A solution of 20% piperidine (Sigma-Aldrich) in N, N-dimethylformide (DMF; Caledon Laboratories) was used for the deprotection step in the synthesis cycle. The DMF was purified in-house and used fresh each time as a solvent for the synthesis. The cleavage/deprotection of the final peptide was carried out with trifluoroacetic acid (TFA), thioanisole, 1, 2 ethandithiol, m-cresole, triisopropylsilane, and bromotrimethyl silane (Sigma-Aldrich) at a ratio of 0:10:5:1:1:5. Finally, it was desalted on a Sephadex G-10 column using aqueous 0.1% TFA solution and lyophilized.

Animals

All animal studies for Example 1 were performed in Canada and followed the requirements set out by the Canadian Council for Animal Care (CCAC) and were approved by the University Animal Care Committee (UACC).

Male adult Sprague-Dawley rats (~350 g) treated for 3 months (1 injection/week) with either vehicle (0.9% saline) or TCAP-1 (25 nmoles/kg) were used in Example 1.

All animal studies for Examples 3 and 4 were performed in Finland by Charles River and Examples 5-7 were performed in Lexington Mass. by Neosome Life Sciences. All animal studies were performed in accordance with applicable animal care standards (e.g. Institutional Animal Care and Use Committee). Animals and amounts to TCAP-1 were used as indicated in the Examples.

Statistics

Tests were used to assess statistical significances. Student's t-test and ANOVAs were used unless specifically stated otherwise. Statistics were denoted by $*p<0.05$, $p<0.01$, $*p<0.001$, $****p<0.0001$.

Example 1: Open Field Test in Stressor Environment of TCAP-1 Treated Animals

Behaviour—Modified Open Field Test

The Open Field Test is a behavioral test paradigm used to investigate anxiety-related behaviours in rodents (Bailey K R and Crawley J N, 2009, in: Buccafusco J J, editor. Source Methods of Behavior Analysis in Neuroscience. 2nd edition. Boca Raton (Fla.): CRC Press/Taylor & Francis; 2009. Chapter 5.). In this experiment, the animals were exposed to high frequency noise pollution to induce a stress response while the animals were in the OFT apparatus. The test was performed one week post last injection of the long-term (3 month) treatment with either vehicle (0.9% saline) or TCAP-1 (25 nmoles/kg). Animals were individually placed in a plexiglass box (50 L×50 W) and digitally recorded and tracked for five (5) minutes. In the centre of the box is a designated section termed the centre zone. Behaviours are then analyzed from videos and recorded for time spent in centre zone, distance travelled in centre zone, and total distance travelled. Moreover, peering behaviour, grooming behaviour, and rearing behaviour were also analyzed (definitions below).

(a) Peering: Digital recordings were analyzed for Peering behaviour. Peering behaviour was defined as the specific notion where animals would stand on their back hind limbs in order to look over the side of the glass wall (i.e, The event where an animal rears specifically to peer over the side of the apparatus). This behaviour can be interpreted as an explorative or anti-fear response.

(b) Grooming: Digital recordings were analyzed for Grooming behaviour. Grooming behaviour was defined as the animals cleaning their face or bodies, i.e., the event where an animal grooms himself (usually his hands and face).

(c) Rearing: Digital recordings were analyzed for Rearing behaviour. Rearing behaviour was defined as an event where animals stand on their hind limbs (i.e., the event where an animal gets on his hind limbs in exploration). This behaviour is interpreted as an explorative behaviour, which is a low anxiety response.

Open Field Test Results

Figure 4:
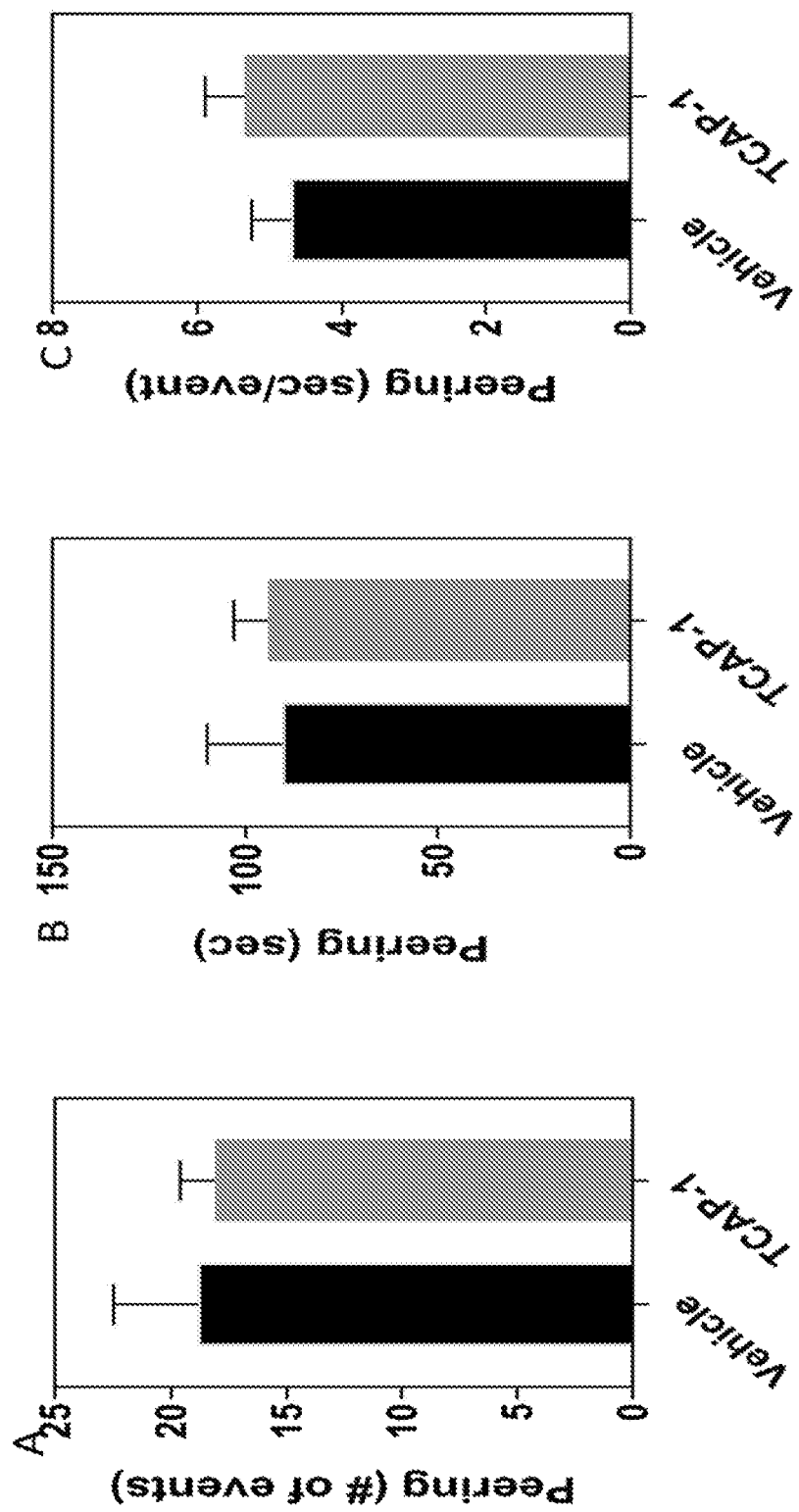
FIG. 4 are bar graphs of the peering behaviour of animals treated with vehicle and TCAP-1 respectively, wherein (A) is the number of events of the peering behaviour; (B) is the time in seconds of the peering behaviour; and (C) is seconds per event of the peering behaviour.
Figure 5:
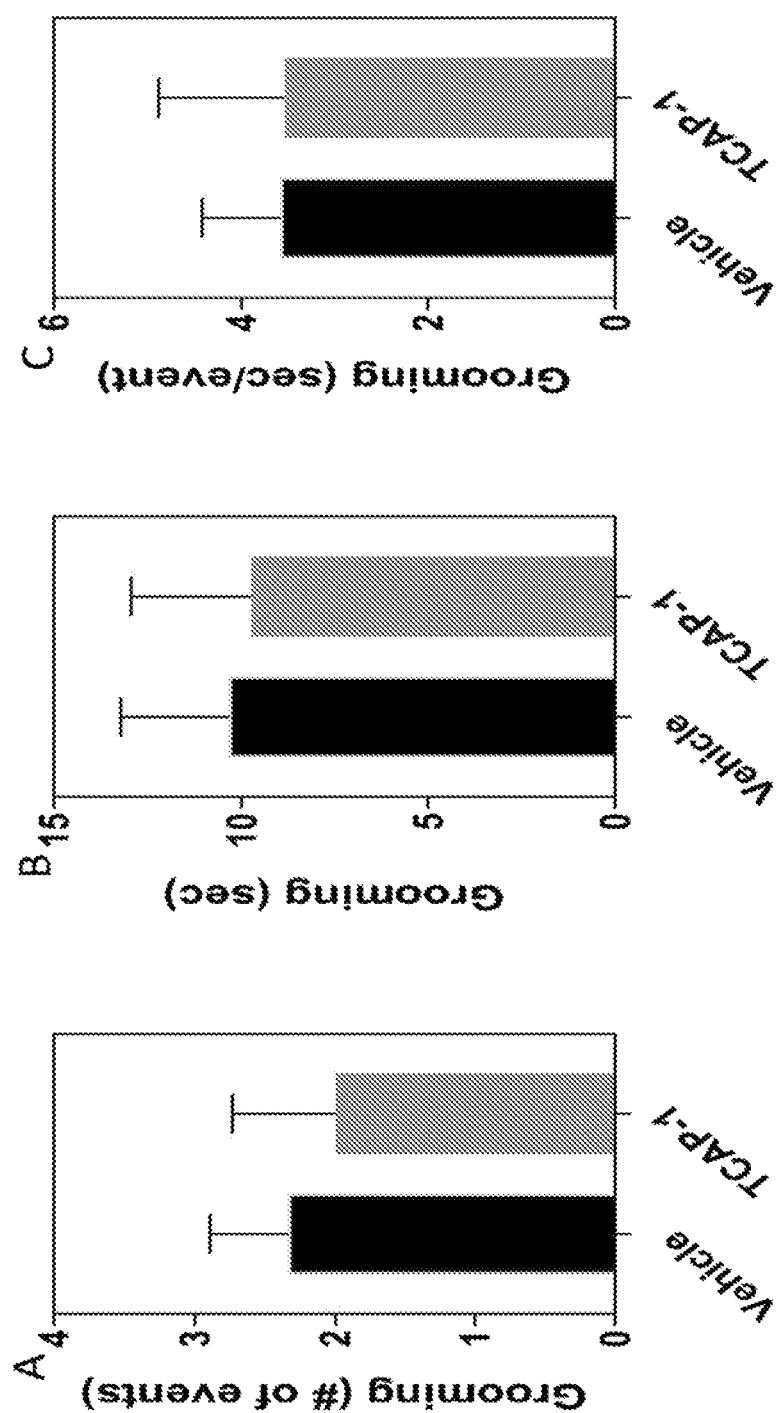
FIG. 5 are bar graphs of the grooming behaviour of animals treated with vehicle and TCAP-1 respectively, wherein (A) is the number of events of the grooming behaviour; (B) is the time in seconds of the grooming behaviour; and (C) is seconds per event of the grooming behaviour.
Figure 6:
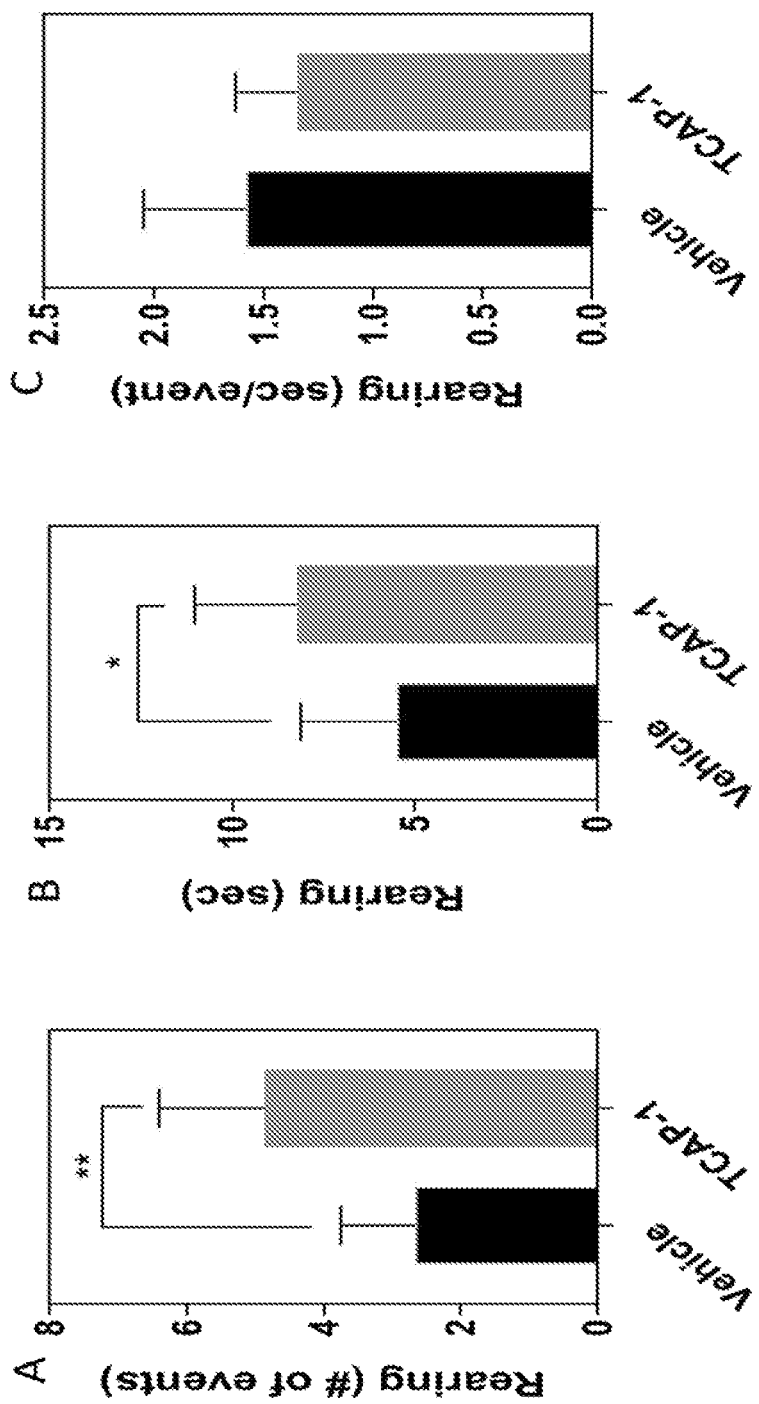
FIG. 6 are bar graphs of the rearing behaviour of animals treated with vehicle and TCAP-1 respectively, wherein (A) is the number of events of the grooming behaviour; (B) is the time in seconds of the grooming behaviour; and (C) is seconds per event of the grooming behaviour.

Animals were digitally recorded and tracked for five (5) minutes in the Open Field Test with noise pollution. The noise pollution was large construction noise, intermittent and not at predictable intervals. First, as shown in FIGS. 2 and 3, TCAP-1 treated group collectively on average spent significantly more time in the centre zone as well as had more entries into centre zone. This indicates that the TCAP-1 treated group is exhibiting a less-anxious response the noise pollution-induced stress response, as well as the novelty of the apparatus. Animals exhibiting anxiety avoided the centre zone, as they often stay to the outsides of the box. Moreover, as illustrated in FIGS. 4-6, peering behaviour and grooming behaviour were not found to be significantly different between groups, however the rearing behaviour was significantly increased in TCAP-1 treated animals. As rearing behaviour is highly associated with anti-anxious behaviour, this corroborates the data indicating TCAP-1 is reducing stress-related behaviour. Importantly, TCAP-1 and vehicle-treated animals did not differ in the total amount of distance traveled within the box, which shows they do not differ in their spontaneous locomotor behaviour, demonstrating this is a neurological-based change in behaviour. As such, chronic TCAP-1 administration significantly decreased stress-related behaviour in the Open Field Test with noise pollution.

Example 2—Clinical Trials in a PTSD Model

PTSD Animal Models:

While TCAP-1 has a definite pharmacological effect in animal behavioral studies additional behavioral studies can be conducted for in specific PTSD models. Additional studies on the effects of TCAP-1 in animal models specifically focused on PTSD (i.e., developed novel behavioral models pertaining to addiction and PTSD) are described herein (including Examples 3-7). For a description of some animal models see Borghans, B. et al., "Animal Models for posttraumatic stress disorder: An overview of what is used in research", World J Psychiatry. 2015 Dec. 22; 5(4): 387-396.) and Flandreau, Elizabeth I. et al., "Animal Models of PTSD; A Critical Review, Curr Topics Behav Neurosci (2018) 38:47-68).

PK/PD, Validate the Route of Administration:

TCAP-1 has beneficial actions on a range of stress responses in selected rodent models. Based on the efficacy in these models, GMP-grade TCAP-1 has been synthesized to support toxicology and Phase 1 studies. PTSD animal models can be employed to optimize formulations and delivery routes, as well as dose ranges. Although parenteral (mainly subcutaneous) injection could be an acceptable route of clinical administration, given the severity of PTSD and efficacious doses of TCAP-1, an oral (buccal or sublingual) or intranasal route of administration could be used. Preclinical experience suggests that one or more of these alternative delivery routes is feasible. TCAP-1 pharmacokinetics and pharmacodynamics can be evaluated in the presence of clinically compatible absorption enhancers. An enzyme-linked immunosorbent assay (ELISA) will be employed to measure systemic bioavailability of TCAP-1. However, due to the localized delivery methods, the high vascularization of the nasal and buccal cavities, and the potentially preferential direct action of TCAP-1 on vomeronasal and hypothalamic areas, the utility of selected TCAP-1 formulations can be assessed using a pharmacodynamic efficacy-indicating behavioral model discussed above. Potential biomarkers for PTSD severity and pharmacodynamics markers of TCAP-1 activity can also be determined, including measurements of central and peripheral CRH, other endocrine markers, cerebral blood flow and/or glucose metabolism, and sleep parameters.

Dosing:

Studies can be conducted to support a starting dose in the First in Human Study. TCAP-1 can be screened to rule out potential off-target activity on standardized receptors/ion channels as required by the FDA. The ancillary pharmacology (safety pharmacology) or TCAP-1 can be determined in rats and monkeys, to detect any unanticipated deleterious pharmacological effects on respiratory, cardiovascular, renal, or nervous system function. Metabolic liability in known standard method using microsomal preparations from various species, including humans can be assessed. TCAP-1's potential for immune or allergic reactions to determine safety and potential liabilities of administering TCAP-1 can also be assessed. Dose-Range-Finding Toxicology studies can be conducted, to select the final optimal dosing regimens in rats and monkeys. This can lead to GLP toxicology studies in rats and monkeys, following one-month of daily subcutaneous administration of TCAP-1 according to FDA guidelines.

Initiation of Human Clinical Trials:

The protocol for a robust, placebo-controlled Phase 1 study in male PTSD patients 18-65. This inpatient trial could be conducted at one to three Phase 1 center(s) in the United States, such as the Veterans Administration (VA) system. The trial can employ a 3+3 design, escalating dose by half-log until dose limiting adverse effects are observed. Following this, the cohort just below that with the dose limiting effect can be expanded. This method can continue until a sizable cohort (8-10 completed patients) at the observed treatment dose is accomplished. The overall study duration is estimated to be 12 months, from First Patient In. A Single Ascending Dose (SAD) trial can be conducted, with patients observed for one week as in-patients and then reassessed at 2 and 4 weeks. A Multiple Ascending Dose Phase 1 trial, also in PTSD patients, can be initiated in a staggered manner, starting a half-log back from the last safe dose in the SAD. This can be followed by a Dose Expansion phase with up to 24 pts. at the treatment dose. The inpatient Observation period would be 2-4 weeks, with out-patient follow up at 6 and 8 weeks. Dosing can be reduced or if needed, the dosing strategy revisited. Biomarkers can include both Pharmacokinetic and Pharmacodynamic endpoints including blood and urine chemistries, screening, baseline and treatment psychological assessments, patient reported outcomes and a sub study cohort in the expansion phase that will include neuroimaging. Sleep studies at baseline and during treatment can also be conducted.

Example 3—Chronic Social Defeat Model in Mice

Figure 7:
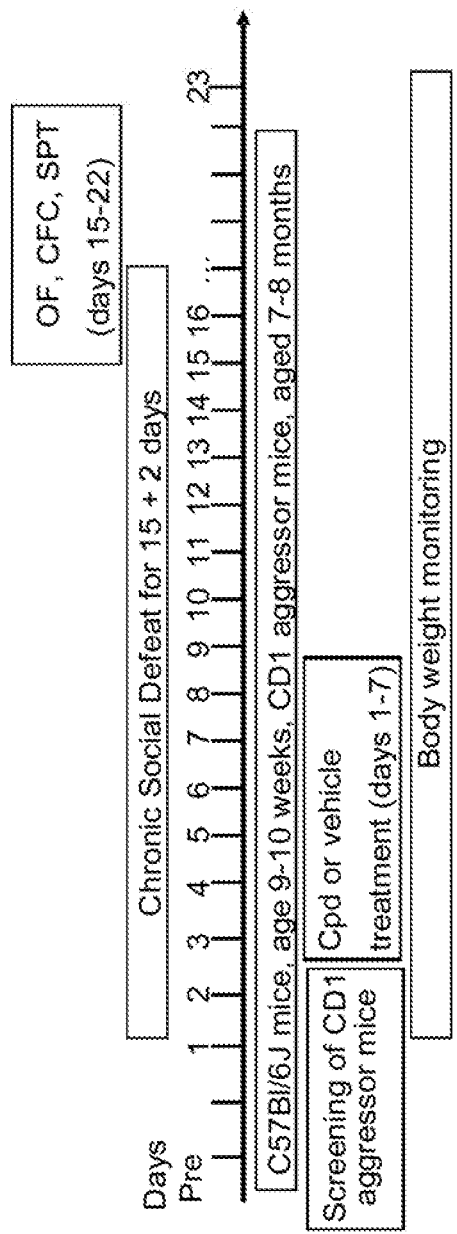
FIG. 7 illustrates the schematic design of the study of Example 3.

The mouse chronic social defeat ("CSD") model has been accepted as a model of PTSD [Flandreau, et al, 2018]. This model involves exposure of C57Bl/6J mice to chronic stress by aggressor mice (male CD-1 ex-breeders) for a defined period of 15 days. Starting from day 15, mice were further tested in the open field (OF) model. A schematic design of the study is shown in FIG. 7.

Experimental Set Up of Mice.

CD-1 mice were housed, one mouse per cage, during the experiments. C57Bl/6J mice were housed in pairs while not subjected to CSD. Mice are acclimated to the animal facility for minimum 5 days before the onset of the study.

CD-1 aggressor mice are determined by using the procedures by Golden et al. (2011). Screening involves three days of selection testing. After the screening and selection of 80 aggressor mice, the chronic social defeat (CSD) paradigm was conducted.

The CSD mouse group were subcutaneously injected once a day with vehicle or TCAP-1 days 1-7.

Under dim lighting a CSD mouse was subjected to direct exposure with a CD-1 aggressor mouse. The behavioural responses were observed with the durations of each physical attack measured; mice were kept together until either cumulative total of 60 sec physical attack, or 10 min had elapsed. The latency to the first attack was also recorded, and time needed to gain 60 s physical attack time. After the 10 min session, CSD mice were exposed to CD-1 mice through perforated transparent divider for 24 h. If the CD-1 mice are very aggressive (if wounding consistently exceeds veterinary guidelines), the exposure time can be shortened to 5 min or less.

This setup allows direct and continued olfactory, visual, auditory exposure for the rest of the day. On the following day, a CSD mouse is placed in a cage in similar fashion with 10 min direct exposure followed by chronic exposure through divider. Cycle is repeated for 15 days, replacing the CSD mouse with a new one every day until day 15. Thereafter, CSD mice remain caged next to the same CD-1 mice without any further attack sessions or rotations for days 16-17.

Figure 8:
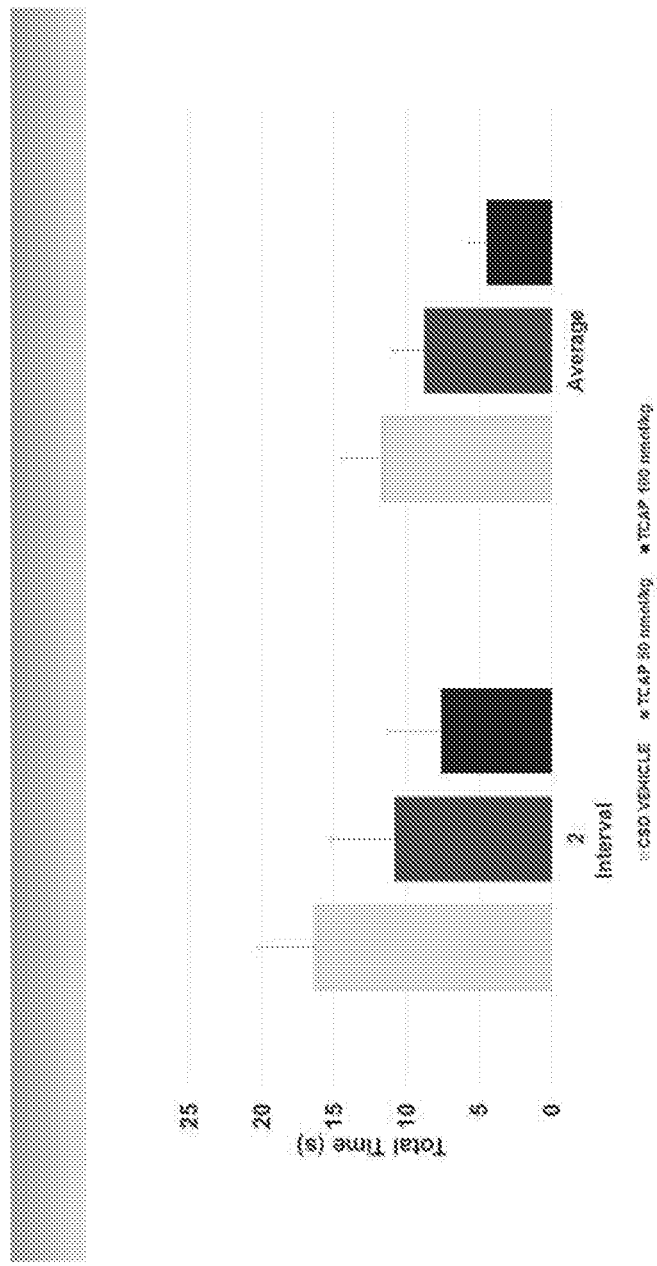
FIG. 8 is bar graph illustrating the attack latency results of Example 3, wherein "time between retreat and evaluating the predator" is on the y-axis.
Figure 9:
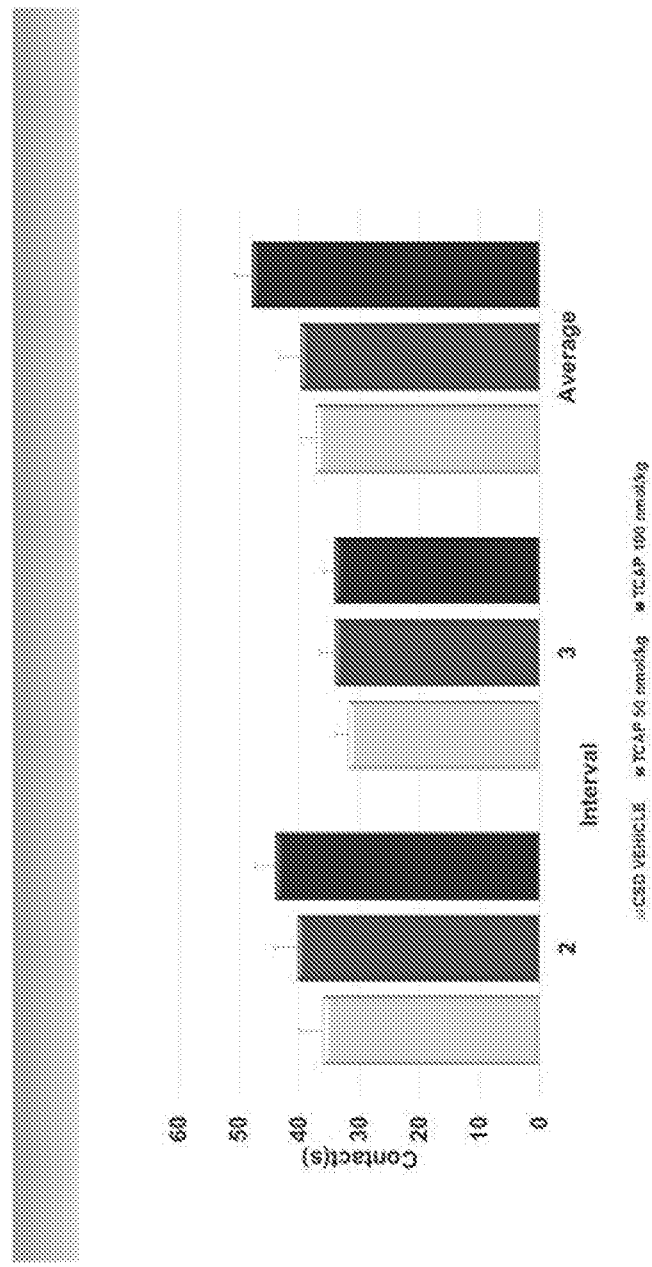
FIG. 9 is a bar graph illustrating aggressive contact time results of Example 3, wherein the time on the y-axis reflects the number of direct contacts wherein the animal will approach the predator and not retreat.

In FIG. 8 it was observed the CSD test mice receiving TCAP-1 lost their inhibition and attack latency increased along with aggressive contact time (FIG. 9). Attack latency is the period between retreat and confrontation. In the model, the administration of TCAp-1 reduces the time between retreat and evaluating the predator as can be seen in FIG. 8. Aggressive contact time reflects the number of direct contacts. FIG. 9 illustrates that administration of TCAP-1, the animal will approach the predator and not retreat.

Example 4—Open Field Test

Behavioral tests such as Open field motor activity (OF) were also conducted. See the schematic of FIG. 7.

In this model set up the test was conducted 15 days after the last CSD session. The mouse was placed on the Open Field apparatus floor in the center of empty arena for 15 min without exposure to any other stimuli. The following parameters were calculated from the data: distance moved, number of vertical rearing's, velocity and % resting time (no movement activity). Open field activity chambers (Med Associates Inc, St Albans, Vt.; 27×27×20.3 cm) are equipped with IR beams with red light conditions. A mouse is considered to have no movement activity when the mouse is not breaking two adjacent beams consecutively (distance between two adjacent beams is about 1.7 cm).

Figure 10:
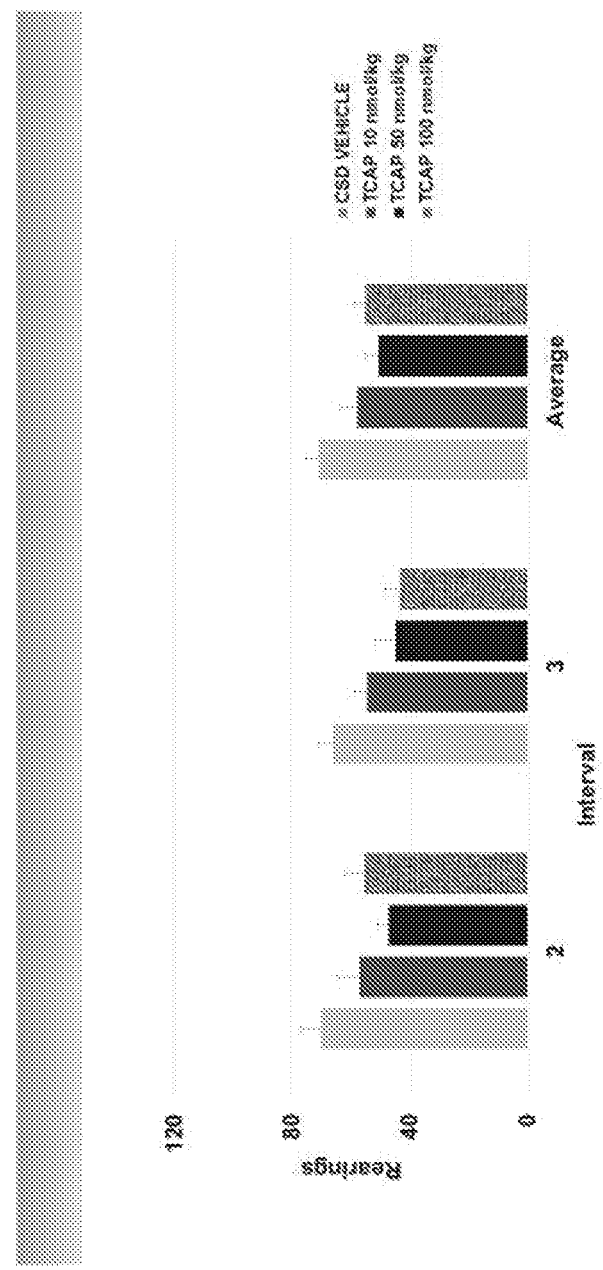
FIG. 10 is a bar graph illustrating the Open Field Rearing test results of Example 4, wherein the y-axis is number of rearings.
Figure 11:
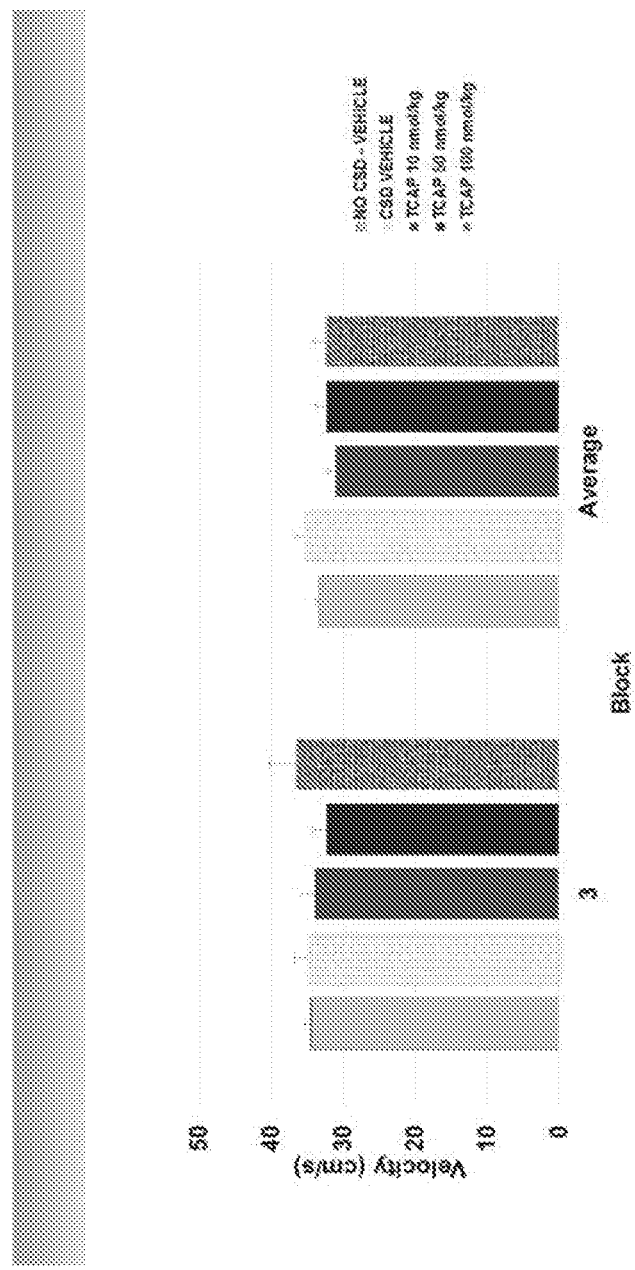
FIG. 11 is a bar graph illustrating the Open Field Velocity test results of Example 4, wherein the y-axis is the velocity of mice.

In the open field study FIGS. 10 and 11, TCAP-1 treated mice were found to display reduced anxiety toward their surroundings and reduced rearing events were observed. It would suggest the animal was less traumatized to its surroundings. The reduction in rearing activity was not due to changes in locomotor activity (LMA) since all groups moved similar distances. Rearings reflect the rodents evaluation of the surroundings. Normally there is a period of anxiety, however TCAP-1 treated animals are less concerned and sample the environment less (FIG. 10). Velocity of mice reflects motion and the results as shown in FIG. 11 illustrate that TCAP-1 treated mice do not have impaired locomotor activity.

Example 5—CRH Driven Rodent Model 1

In one model, Swiss Webster mice were stressed following chronic opiate administration. It was determined that TCAP efficiently modulated the symptomology of precipitated withdrawal whereas a small molecule CRH antagonist had limited success.

Figure 12:
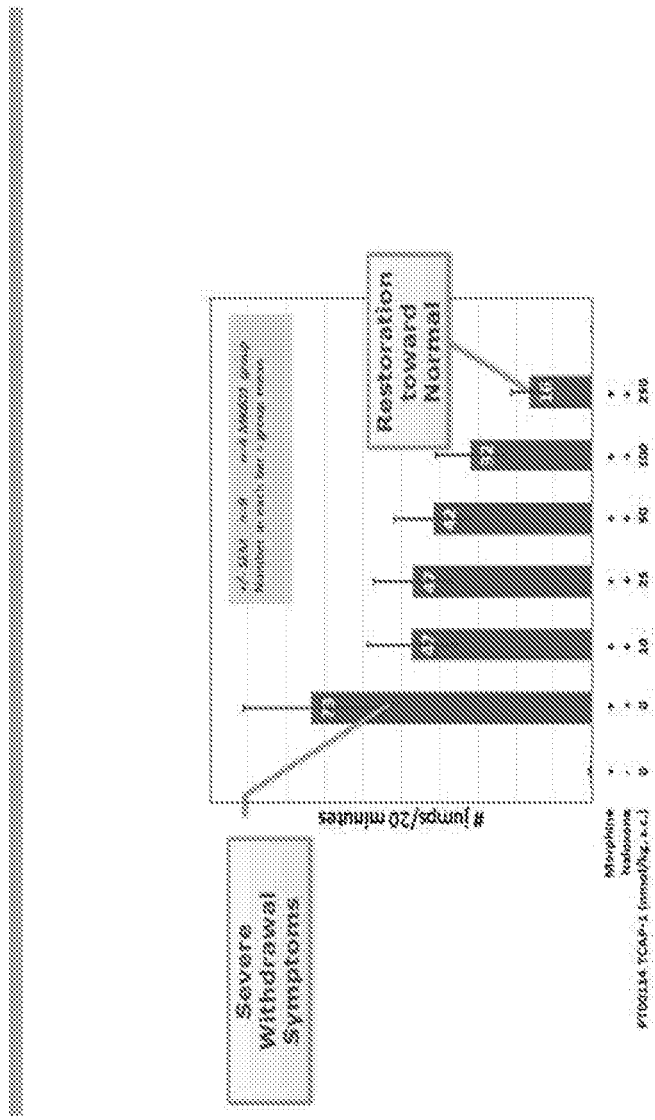
FIG. 12 is a bar graph illustrating the saelens drug-precipitated withdrawal stress response in mice of Example 5, where the y-axis is the number of jumps per 20 minutes and the x-axis illustrates the treatments (morphine, naloxone and TCAP-1).

FIG. 12 demonstrates a dose dependent reduction in jumping activity following the administration of naloxone.

In this Example, TCAP-1 was administered at the graded doses, daily for three days prior to administration of morphine. Morphine was then administered at 3.2 mg/kg i.p. on day 4 (5 times) and 5 (twice), and then one hour the last dose of morphine, naloxone is administered i.p at 10 mg/kg, to induce withdrawal.

One hour after last morphine treatment (i.e. after administration of Naloxone) the mice were immediately placed individually in an observation area and video recorded 20 minutes. The number of jumps (lifting of all feet off the ground) documented for 20 minutes Example 6—CRH Driven Rodent Model 2

A similar study was performed using a CRH antagonist (CP154, 526) in the precipitated withdrawal model.

Male, Swiss Webster mice were treated with seven (7) doses of Morphine 3.2 mg/kg i.p. (d1×5 and d2×2). Animals were then administered a test substance subcutaneously one hour after the last morphine injection with either: (i) nothing (morphine only); (ii) CRH antagonist (CP154, 526) or (iii) TCAP-1 and then an hour after the test substance the animals were administered naloxone i.p at 10 mg/kg, to induce withdrawal.

Two hours after last morphine treatment (i.e. after administration of Naloxone) the mice were immediately placed individually in an observation area and video recorded 20 minutes. The number of jumps (lifting of all feet off the ground) documented for 20 minutes.

Figure 13:
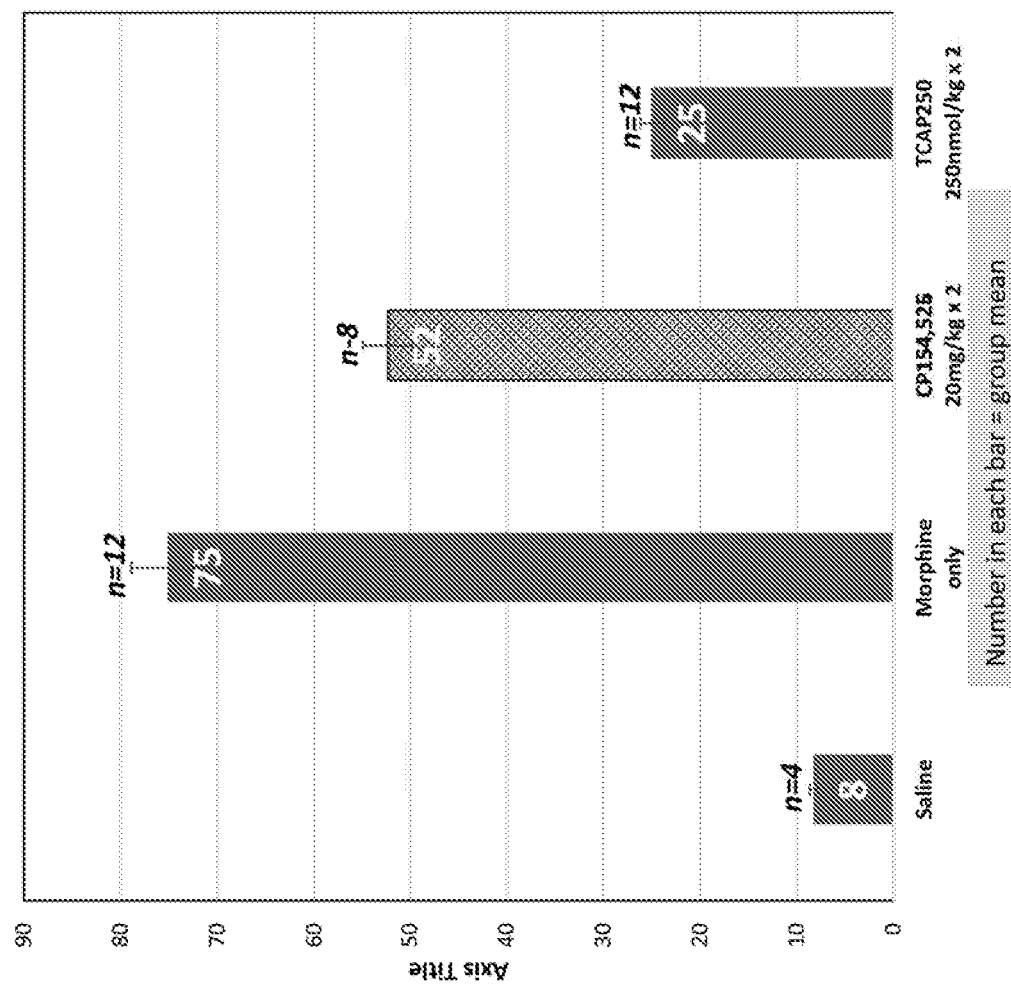
FIG. 13 is a bar graph illustrating the saelens drug-precipitated withdrawal stress response in mice of Example 6, where the y-axis is the number of jumps per 20 minutes and the x-axis illustrates the treatments (morphine only, CP154, 526 and TCAP-1).

FIG. 13 demonstrates the efficacy of TCAP-1 at 250 nmole/Kg versus the small molecule CRH antagonist (CP154, 526) administered at 20 mg/Kg. (For description on CP154, 526 see for example, CNS Drug Reviews, Vol. 9, No. 1, pp 57-96, Seymour, Patricia A., et al, "The Pharmacology of CP-154,526, A Non-Peptide Antagonist of the CRH1 Receptor: A Review, incorporated herein by reference.)

Example 7—Restraint Stress Model

The inventors, extended the behavioural activity in a severe restraint model the changes in a stress related biomarker such as corticosterone is depicted in FIG. 14. (See for example de Pablos, R. N. et al (2014), Creating a Rat model of Chronic Variate Stress. *Bio-protocol* 4(23): e1315.DOI).

In this model animals, Swiss Webster mice (SW) (FIG. 14 A) and Sprague-Dawley rat (SD) (FIG. 14 B) were restrained in confined spaces for upwards of 30-60 minutes on successive days. TCAP-1 was administered once at day 1 and at day 2 in the 5-day model. The administration of TCAP-1 modulated the rise in corticosterone in 5 days in the mouse and within 3 days in the rat.

While the foregoing invention has been described in some detail for purposes of clarity and understanding, it will be appreciated by one skilled in the art, from a reading of the disclosure, that various changes in form and detail can be made without departing from the true scope of the invention in the appended claims.

All publications, patents, and patent applications are herein incorporated by reference in their entirety to the same extent as if each individual publication, patent or patent application was specifically and individually indicated to be incorporated by reference in its entirety.

REFERENCES

American Psychiatric Association (2013). Diagnostic and Statistical Manual of Mental Disorders (Fifth ed.). Arlington, Va.: American Psychiatric Publishing.
Nair, Arnroop B. and Jacob, Shery, J Basic Clin Pharm. March 2016-May 2016; 7(2): 27-31
Al Chawaf, A., Xu, K., Tan, L., Vaccarino, F. J., Lovejoy, D. A., & Rotzinger, S. (2007). Corticotropin-releasing factor (CRF)-induced behaviors are modulated by intravenous administration of teneurin C-terminal associated peptide-1 (TCAP-1). http://doi.org/10.1016/j.peptides.2007.05.014
Bailey K R and Crawley J N, 2009, in: Buccafusco J J, editor. Source Methods of Behavior Analysis in Neuroscience. 2nd edition. Boca Raton (Fla.): CRC Press/Taylor & Francis; 2009. Chapter 5
Bellinger, A. M., Mongillo, M., & Marks, A. R. (2008). Review series Stressed out: the skeletal muscle ryanodine receptor as a target of stress. Journal of Clinical Investigation, 118(2), 445-453. http://doi.org/10.1172/JCI34006.effects
Borghans, B. et al., "Animal Models for posttraumatic stress disorder: An overview of what is used in research", World J Psychiatry. 2015 Dec. 22; 5(4): 387-396.)
Boucard, A. A., Maxeiner, S., & Sudhof, T. C. (2014). Latrophilins function as heterophilic cell-adhesion molecules by binding to teneurins: Regulation by alternative splicing. Journal of Biological Chemistry, 289(1), 387-402. http://doi.org/10.1074/jbc.M113.504779
Chand, D., Casatti, C. A., de Lannoy, L., Song, L., Kollara, A., Barsyte-Lovejoy, D., . . . Lovejoy, D. A. (2013). C-terminal processing of the teneurin proteins: Independent actions of a teneurin C-terminal associated peptide in hippocampal cells. Molecular and Cellular Neuroscience, 52, 38-50. http://doi.org/10.1016/j.mcn.2012.09.006
Chen, Y., Xu, M., Almeida, R. De, & Lovejoy, D. A. (2013). Teneurin C-terminal associated peptides (TCAP): Modulators of corticotropin-releasing factor (CRF) physiology and behavior. Frontiers in Neuroscience, 7(7 SEP), 1-6. http://doi.org/10.3389/fnins.2013.00166
Committee on the Assessment of Ongoing Efforts in the Treatment of Posttraumatic Stress Disorder; Board on the Health of Select Populations; Institute of Medicine. Washington (DC): National Academies Press (US); 2014 Jun. 17.
Davletov, B. A., Meunier, F. A., Ashton, A. C., Matsushita, H., Hirst, W. D., Lelianova, V. G., . . . Ushkaryov, Y. A. (1998). Vesicle exocytosis stimulated by α-latrotoxin is mediated by latrophilin and requires both external and stored Ca2+. EMBO Journal, 17(14), 3909-3920. http://doi.org/10.1093/emboj/17.14.3909
de Pablos, R. N. et al (2014), Creating a Rat model of Chronic Variate Stress. *Bio-protocol* 4(23): e1315.DOI
Flandreau, Elizabeth I. and Toth, Mate, "Animal Models of PTSD; A Critical Review", Curr Topics Behav Neurosci (2018) 38:47-68
Gennaro, ed., Remington: The Science and Practice of Pharmacy, 20th Ed. (Lippincott Williams & Wilkins 2003).
Golden, Sam A.; Covington, Herbert E; Burton, Olivier; Russo, Scott J., "A standardized protocol for repeated social defeat stress in mice", Nat Protoc. 2011 Jul. 21; 6(8): 1183-1191
Harnett N G, Wood K H, Ference E W 3rd, Reid M A, Lahti A C, Knight A J, Knight D C. 2017. Glutamate/glutamine concentrations in the dorsal anterior cingulate vary with Post-Traumatic Stress Disorder Symptoms. J Psychiatr Res. 91:169-176.
Holmes S E, Girgenti M J, David M T, Pietrzak R H, DellaGioia N, Nabulsi N, Matuskey D et al. 2017. Altered metabotropic glutamate receptor 5 markers in PTSD: In vivo and postmortem evidence. Proc Natl Acad Sci USA. 114(31): 8390-8395.
Kenzelmann, D., Chiquet-Ehrismann, R., & Tucker, R. P. (2007). Teneurins, a transmembrane protein family involved in cell communication during neuronal development. Cellular and Molecular Life Sciences, 64(12), 1452-1456. http://doi.org/10.1007/s00018-007-7108-9
Kupferschmidt, D. A., Lovejoy, D. A., Rotzinger, S., & Erb, S. (2011). Teneurin C-terminal associated peptide-1 blocks the effects of corticotropin-releasing factor on reinstatement of cocaine seeking and on cocaine-induced behavioural sensitization. British Journal of Pharmacology, 162(3), 574-583. http://doi.org/10.1111/j.1476-5381.2010.01055.x Maher, F., Davies-Hill, T. M., Lysko, P. G., Henneberry, R. C., & Simpson, I. a. (1991). Expression of two glucose transporters, GLUT1 and GLUT3, in cultured cerebellar neurons:
Evidence for neuron-specific expression of GLUT3. Molecular and Cellular Neurosciences, 2(4), 351-60. http://doi.org/10.1016/1044-7431(91)90066-W Martin, E. W., ed, "Remington's Pharmaceutical Sciences", 18.sup.th Edition.

Minet, a D., Rubin, B. P., Tucker, R. P., Baumgartner, S., & Chiquet-Ehrismann, R. (1999). Teneurin-1, a vertebrate homologue of the *Drosophila* pair-rule gene ten-m, is a neuronal protein with a novel type of heparin-binding domain. Journal of Cell Science, 112 (Pt 1, 2019-2032.

Nair, Arnroop B. and Jacob, Shery, J Basic Clin Pharm. "A simple practice guide of dose conversion between animals and human". March 2016-May 2016; 7(2): 27-31

Rosso I M, Crowley D J, Silveri M M, Rauch S L, Jensen J E. 2017. Hippocampus glutamare and n-acetyl aspartate markers of excitotoxic neuronal compormise in posttraumatic stress disorder. Neuropsychopharmacology. 41(8): 1698-1705.

Silva, J.-P., Lelianova, V. G., Ermolyuk, Y. S., Vysokov, N., Hitchen, P. G., Berninghausen, O., . . . Ushkaryov, Y. A. (2011). Latrophilin 1 and its endogenous ligand Lasso/teneurin-2 form a high-affinity transsynaptic receptor pair with signaling capabilities. Proceedings of the National Academy of Sciences of the United States of America, 108(29), 12113-8. http://doi.org/10.1073/pnas.1019434108

Tan, L. A., Al Chawaf, A., Vaccarino, F. J., Boutros, P. C., & Lovejoy, D. A. (2011). Teneurin C-terminal associated peptide (TCAP)-1 modulates dendritic morphology in hippocampal neurons and decreases anxiety-like behaviors in rats. Physiology and Behavior, 104(2), 199-204. http://doi.org/10.1016/j.physbeh.2011.03.015

Tan, L. A., Xu, K., Vaccarino, F. J., Lovejoy, D. A., & Rotzinger, S. (2009). Teneurin C-terminal associated peptide (TCAP)-1 attenuates corticotropin-releasing factor (CRF)-induced c-Fos expression in the limbic system and modulates anxiety behavior in male Wistar rats. Behavioural Brain Research, 201, 198-206. http://doi.org/10.1016/j.bbr.2009.02.013

Trubiani, G., Al Chawaf, A., Belsham, D. D., Barsyte-Lovejoy, D., & Lovejoy, D. A. (2007). Teneurin carboxy (C)-terminal associated peptide-1 inhibits alkalosis-associated necrotic neuronal death by stimulating superoxide dismutase and catalase activity in immortalized mouse hypothalamic cells. Brain Research, 1176(1), 27-36. http://doi.org/10.1016/j.brainres.2007.07.087

Wang, L., Rotzinger, S., Al Chawaf, A., Elias, C. F., Barsyte-Lovejoy, D., Qian, X., . . . Lovejoy, D. A. (2005). Teneurin proteins possess a carboxy terminal sequence with neuromodulatory activity. Molecular Brain Research, 133(2), 253-265. http://doi.org/10.1016/j.molbrainres.2004.10.019

Woelfle, R., D'Aquila, A. L., Pavlovic, T., Husic, M., Lovejoy, D. A. (2015). Ancient interaction between the teneurin C-terminal associated peptides (TCAP) and latrophilin ligand-receptor coupling: a role in behavior, 9(April), 1-10. http://doi.org/10.3389/fnins.2015.00146

Yehuda R, Halligan S L, Golier J A, Grossman R, Bierer L M (2004). "Effects of trauma exposure on the cortisol response to dexamethasone administration in PTSD and major depressive disorder". Psychoneuroendocrinology. 29 (3): 389-404.

Yehuda R, Halligan S L, Grossman R, Golier J A, Wong C (2002). "The cortisol and glucocorticoid receptor response to low dose dexamethasone administration in aging combat veterans and holocaust survivors with and without posttraumatic stress disorder". Biol Psychiatry. 52 (5): 393-403.

What is claimed is:

1. A method for treating post-traumatic stress disorder in a subject in need thereof comprising administering to the subject a therapeutically effective amount of a teneurin c-terminal associated peptide-1 (a TCAP-1 peptide), or a pharmaceutically acceptable salt or ester thereof or a pharmaceutical composition comprising the same, wherein the amino acid sequence of said TCAP-1 peptide consists of:
   an amino acid sequence of SEQ ID NOs: 1, 2, or 3; or having at least 95% identity to an amino acid sequence selected from the group consisting of SEQ ID NOs: 1, 2 and 3;
   wherein:
   (a) the carboxy terminal end of said peptide is amidated or comprises an amidation signal sequence; and
   (b) the amino terminal amino acid of said peptide is a glutamine, the glutamine being in the form of pyroglutamic acid.

2. The method of claim 1, wherein the TCAP-1 peptide is SEQ ID NO: 1, wherein:
   (a) the carboxy terminal end of said peptide is amidated or comprises an amidation signal sequence; and
   (b) the amino terminal amino acid of said peptide is a glutamine, the glutamine being in the form of pyroglutamic acid.

3. The method of claim 1, wherein the TCAP-1 peptide is SEQ ID NO: 2, wherein:
   (a) the carboxy terminal end of said peptide is amidated or comprises an amidation signal sequence; and (b) the amino terminal amino acid of said peptide is a glutamine, the glutamine being in the form of pyroglutamic acid.

4. The method of claim 1, wherein the subject is a human.

5. The method of claim 1, wherein the treatment reduces trauma in response to their surroundings experienced in the subject.

6. The method of claim 1, wherein the treatment reduces anxiety in response to their surroundings experienced in the subject.

* * * * *